US00PP16101P2

(12) United States Plant Patent
Snijder

(10) Patent No.: US PP16,101 P2
(45) Date of Patent: Nov. 8, 2005

(54) ***GERANIUM* PLANT NAMED 'FISUM PINK'**

(50) Latin Name: *Pelargonium×hortorum*
Varietal Denomination: Fisum Pink

(75) Inventor: Ronald Snijder, De Lier (NL)

(73) Assignee: Fides Goldstock Breeding B.V., De Lier (NL)

( * ) Notice: Subject to any disclaimer, the term of this patent is extended or adjusted under 35 U.S.C. 154(b) by 22 days.

(21) Appl. No.: 10/959,785

(22) Filed: Oct. 6, 2004

(51) Int. Cl.[7] ..... A01H 5/00
(52) U.S. Cl. ..... Plt./327
(58) Field of Search ..... Plt./327

*Primary Examiner*—Kent Bell
(74) *Attorney, Agent, or Firm*—C. A. Whealy

(57) ABSTRACT

A new and distinct cultivar of Zonal *Geranium* plant named 'Fisum Pink', characterized by its upright and rounded plant habit; moderately vigorous growth habit; freely branching and flowering habit; salmon pink-colored flowers arranged in rounded umbels held above and beyond the foliage on moderately strong peduncles; and good garden performance.

1 Drawing Sheet

Botanical classification/cultivar designation: *Pelargonium×hortorum* cultivar Fisum Pink.

BACKGROUND OF THE INVENTION

The present invention relates to a new and distinct cultivar of Zonal *Geranium* plant, botanically known as *Pelargonium×hortorum*, and hereinafter referred to by the name 'Fisum Pink'.

The new Zonal *Geranium* is a product of a planned breeding program conducted by the Inventor in De Lier, The Netherlands. The objective of the breeding program was to develop new Zonal *Geraniums* with uniform plant habit and interesting flower and foliage colors.

The new Zonal *Geranium* originated from a cross-pollination made by the Inventor in 2000 of two unnamed proprietary selections of *Pelargonium×hortorum*, not patented. The cultivar Fisum Pink was discovered and selected by the Inventor as a flowering plant within the progeny from this cross-pollination in a controlled environment in De Lier, The Netherlands.

Asexual reproduction of the new cultivar by terminal cuttings in a controlled environment in De Lier, The Netherlands since 2002 has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Fisum Pink'. These characteristics in combination distinguish 'Fisum Pink' as a new cultivar and distinguish it from other known Zonal *Geranium* cultivars (including the parental selections):

1. Upright and rounded plant habit.
2. Moderately vigorous growth habit.
3. Freely branching and flowering habit.
4. Salmon pink-colored flowers arranged in rounded umbels held above and beyond the foliage on moderately strong peduncles.
5. Good garden performance.

Plants of the new Zonal *Geranium* can be compared to plants of the cultivar Palais, disclosed in U.S. Plant Pat. No. 5,315. In side-by-side comparisons conducted in De Lier, The Netherlands, plants of the new Zonal *Geranium* differed from plants of the cultivar Palais primarily in growth habit as plants of the new *Geranium* were more freely branching than plants of the cultivar Palais.

Plants of the new Zonal *Geranium* can also be compared to plants of the cultivar Bergpalais, not patented. In side-by-side comparisons conducted in De Lier, The Netherlands, plants of the new Zonal *Geranium* differed from plants of the cultivar Bergpalais in the following characteristics:

1. Plants of the new Zonal *Geranium* were more freely branching than plants of the cultivar Bergpalais.
2. Flowers of plants of the new Zonal *Geranium* were more salmon in color than flowers of plants of the cultivar Bergpalais.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a typical flowering plant of 'Fisum Pink' grown in a container.

DETAILED BOTANICAL DESCRIPTION

Plants of the cultivar Fisum Pink have not been observed under all possible environmental conditions. The phenotype may vary somewhat with variations in environment, such as temperature and light intensity, without, however, any variance in genotype.

The aforementioned photograph, following observations, and averaged measurements describe plants grown during the spring in January in 12-cm pots in De Lier, The Netherlands, and grown under commercial practice in a glass-covered greenhouse with day temperatures ranging from 17 to 20° C., night temperatures ranging from 6 to 14°

C., and light levels ranging from 10,000 to 50,000 lux. Plants used for the photograph and the detailed botanical description were about one year old. In the following description, color references are made to The Royal Horticultural Society Colour Chart, 2001 Edition, except where general terms of ordinary dictionary significance are used.

Botanical classification: *Pelargonium×hortorum* cultivar Fisum Pink.

Parentage:

*Female parent.*—Unnamed proprietary selection of *Pelargonium×hortorum*, not patented.

*Male parent.*—Unnamed proprietary selection of *Pelargonium×hortorum*, not patented.

Propagation:

*Type cutting.*—Terminal cutttings.

*Time to initiate roots.*—Summer: About 7 days at 21° C. Winter: About 10 days at 21° C.

*Time to produce a rooted young plant.*—Summer: About 18 to 22 days at 21° C. Winter: About 26 to 30 days at 21° C.

*Root description.*—Fine, freely branching; white in color.

Plant description:

*General appearance.*—Upright and rounded plant habit; uniform; densely foliated.

*Growth and branching habit.*—Moderately vigorous growth habit. Freely branching, about five lateral branches develop without pinching, that is, removal of terminal apices.

*Plant height.*—About 20 cm.

*Plant width.*—About 27 cm.

*Lateral branches.*—Length: About 5.2 cm. Diameter: About 6 mm. Internode length: About 1.5 cm. Texture: Densely pubescent. Strength: Moderately strong. Color: 144B.

*Foliage description.*—Arrangement: Alternate, simple. Length: About 6.6 cm. Width: About 7.9 cm. Shape: Orbicular to reniform. Apex: Rounded acute. Base: Cordate. Margin: Crenate; undulate. Venation pattern: Palmate. Texture, upper surface: Smooth, glabrous. Texture, lower surface: Densely pubescent. Color: Developing foliage, upper surface: 137A; towards the base, 143A; distinct zonation pattern, 147A. Developing foliage, lower surface: 137B to 137C. Fully expanded foliage, upper surface: 137A; distinct zonation pattern, between 147A and N189A. Fully expanded foliage, lower surface: 138A. Venation, upper and lower surfaces: 144A. Petiole: Length: About 6.3 cm. Diameter: About 3 mm. Color, upper and lower surfaces: 143A.

Flower description:

*Flower arrangement.*—Salmon pink-colored, rotate and semi-double flowers arranged in rounded hemispherical umbels arising from apical leaf axils. Umbels displayed above the foliage on moderately strong peduncles. Flowers face upright to outwardly. Umbels persistent, flowers not persistent. Flowers slightly fragrant.

*Quantity of flowers.*—Freely flowering habit; at full flower, plants have at least about five open and developing umbels with about 60 flowers per umbel.

*Flowering season.*—Year-round under greenhouse conditions. In the garden, flowering is continuous from late spring until fall.

*Flower longevity.*—Flowers last about six days on the plant.

*Umbel height.*—About 7.2 cm.

*Umbel diameter.*—About 8.5 cm.

*Flower diameter.*—About 4.3 cm.

*Flower depth (height).*—About 2 cm.

*Flower buds.*—Length: About 1.3 cm. Diameter: About 6 mm. Shape: Elliptic. Color: Towards the base, 144A to 144B; towards the apex, 157D; at the apex, 36D.

*Petals.*—Quantity per flower: About five. Length: About 2.6 cm. Width: About 1.9 cm. Shape: Broadly obovate. Apex: Rounded. Base: Attenuate. Margin: Entire. Texture, upper and lower surfaces: Smooth, glabrous. Color: When opening, upper surface: 43C to 43D. When opening, lower surface: 49D; towards the base, 49A. Fully opened, upper surface: Between 43C and 48B; color does not fade with development. Fully opened, lower surface: 49A. Venation, upper and lower surfaces: Same as petal color.

*Petaloids.*—Quantity per flower: About three. Length: About 2 cm; irregular in size. Width: About 1.1 cm; irregular in size. Shape: Variable, roughly obovate. Apex: Mostly rounded. Base: Attenuate. Margin: Entire. Texture, upper and lower surfaces: Smooth, glabrous. Color: When opening, upper and lower surfaces: 43C to 43D. Fully opened, upper and lower surfaces: Between 43C and 48B; color does not fade with development. Venation, upper and lower surfaces: Same as petaloid color.

*Sepals.*—Quantity per flower: Five, arranged in a single whorl. Length: About 1 cm. Width: About 3 mm. Shape: Lanceolate. Apex: Acute. Base: Cuneate. Margin: Entire. Texture, upper surface: Smooth, glabrous. Texture, lower surface: Densely pubescent. Color, upper and lower surfaces: 144A to 144B.

*Peduncle (umbel stem).*—Length: About 14.3 cm. Diameter: About 4 mm. Angle: About 20° from vertical. Strength: Moderately strong. Texture: Pubescent. Color: 143A.

*Pedicel (individual flower stem).*—Length: About 2.9 cm. Diameter: About 1.5 mm. Angle: About 15° from vertical. Strength: Moderately strong. Texture: Pubescent. Color: 144A to 144B.

*Reproductive organs.*—Androecium: Anther quantity per flower: About five to ten. Anther length: About 2 mm. Anther shape: Narrowly oblong. Anther color: 182B. Filament length: About 7 mm. Filament color: N155A; towards the apex, 47B. Pollen amount: Moderate. Pollen color: N172A to N172B. Gynoecium: Pistil quantity per flower: One. Pistil length: About 3 mm. Stigma shape: Terete; reflexed. Stigma color: 51A. Style length: About 2 mm. Style color: 51A to 51B. Ovary color: 138B.

*Seed/fruit.*—Seed and fruit development has not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from 4 to 40° C. and have good garden performance.

It is claimed:

1. A new and distinct cultivar of Zonal *Geranium* plant named 'Fisum Pink', as herein illustrated and described.

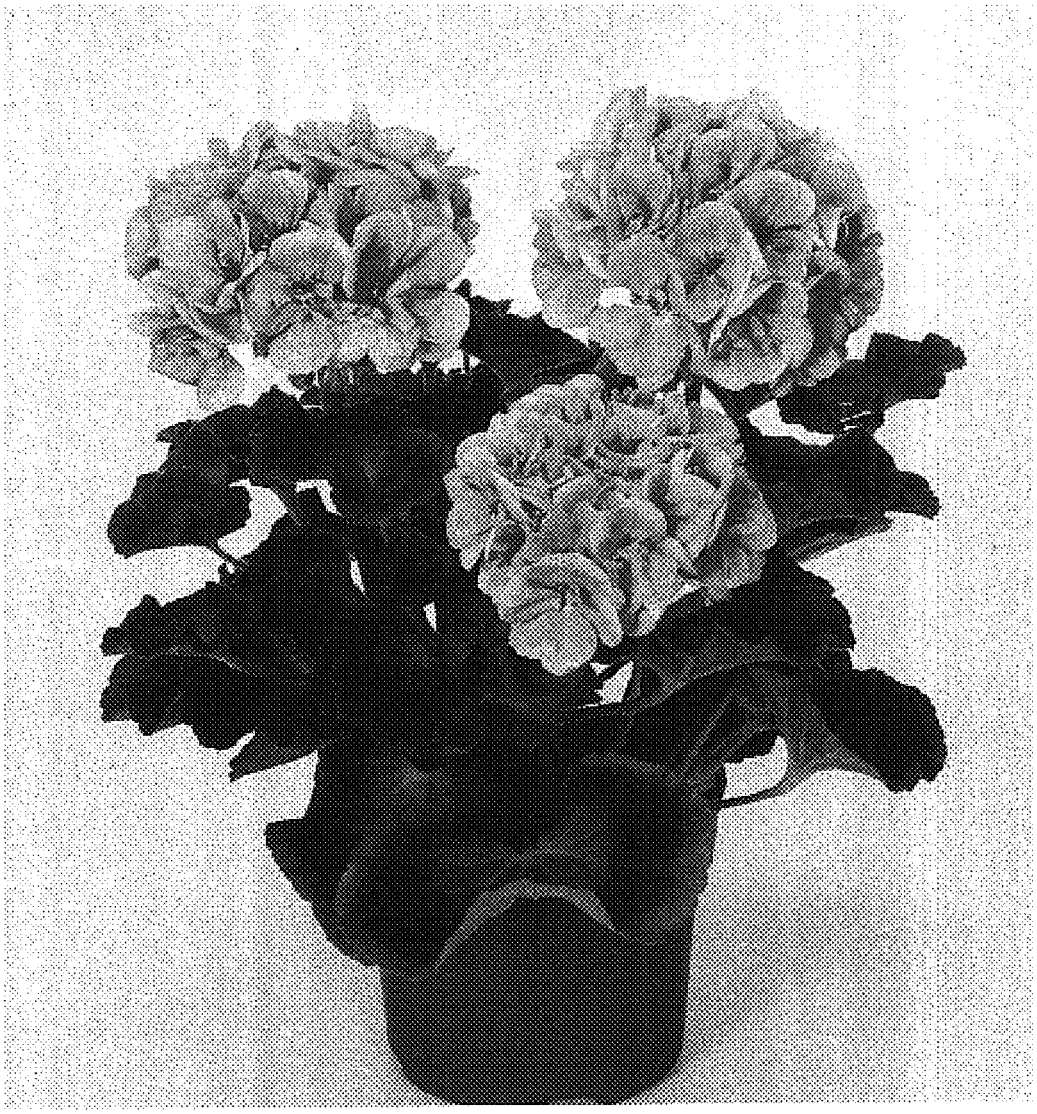

* * * * *